(12) United States Patent
Arlotti et al.

(10) Patent No.: US 12,268,510 B2
(45) Date of Patent: Apr. 8, 2025

(54) APPARATUS AND METHOD FOR TREATING NEUROLOGICAL DISORDERS

(71) Applicant: Newronika S.R.L., Milan (IT)

(72) Inventors: Mattia Arlotti, Rimini (IT); Alberto Priori, Borgo Virgilio (IT); Lorenzo Rossi, Trento (IT)

(73) Assignee: Newronika S.p.A., Milan (IT)

( * ) Notice: Subject to any disclaimer, the term of this patent is extended or adjusted under 35 U.S.C. 154(b) by 1398 days.

(21) Appl. No.: 16/792,098

(22) Filed: Feb. 14, 2020

(65) Prior Publication Data

US 2020/0254261 A1   Aug. 13, 2020

Related U.S. Application Data

(63) Continuation of application No. 15/550,284, filed as application No. PCT/IB2016/050735 on Feb. 11, 2016, now Pat. No. 10,596,379.

(30) Foreign Application Priority Data

Feb. 16, 2015 (IT) ............................ MI2015A000219

(51) Int. Cl.
*A61B 5/374* (2021.01)
*A61B 5/00* (2006.01)
(Continued)

(52) U.S. Cl.
CPC ............ *A61B 5/374* (2021.01); *A61B 5/4076* (2013.01); *A61B 5/4836* (2013.01);
(Continued)

(58) Field of Classification Search
CPC ..... A61B 5/374; A61B 5/4076; A61B 5/4836; A61B 5/4082; A61B 5/7257; G16H 20/30;
(Continued)

(56) References Cited

U.S. PATENT DOCUMENTS

| 5,683,422 | A | 11/1997 | Rise |
| 6,360,122 | B1 | 3/2002 | Fischell et al. |

(Continued)

FOREIGN PATENT DOCUMENTS

| CN | 101589549 A | 11/2009 |
| EP | 2 004 036 B1 | 7/2011 |

(Continued)

OTHER PUBLICATIONS

BioWorld MedTech (2019). Cortera WAND Technology, Clarivate Analytics, 10 total pages.
(Continued)

*Primary Examiner* — Aaron F Roane
(74) *Attorney, Agent, or Firm* — COOLEY LLP (57) ABSTRACT

The present invention concerns an apparatus for treating neurological disorders comprising (i) at least one electrode implantable in the brain of a patient and (ii) a processing and stimulation device connected to the at least one electrode, wherein the processing and stimulation device comprises (a) at least one stimulation module adapted to generate a stimulation signal to be sent to the at least one electrode, the stimulation signal being characterised by a plurality of parameters, (b) at least one acquisition module of a signal characteristic of cerebral activity coming from the brain of the patient adapted to determine its power in at least one frequency band, and (c) at least one control module of at least one parameter of the stimulation signal as a function of the power of the signal characteristic of cerebral activity acquired, based on a transfer function having a saturating trend, wherein the transfer function is such as to set the at least one parameter (Va, Vd, Vf) of the stimulation signal (Vstim) differently dependent on a plurality of power ranges, by keeping the at least one parameter within a predetermined
(Continued)

stimulation range ([Vi_HighThreshold; Vi_LowThreshold]) with i=a,d,f.

8 Claims, 4 Drawing Sheets

(51) Int. Cl.
    *A61N 1/05*           (2006.01)
    *A61N 1/36*           (2006.01)
    *G16H 20/30*         (2018.01)

(52) U.S. Cl.
    CPC ......... *A61N 1/0534* (2013.01); *A61N 1/3606* (2013.01); *A61N 1/36067* (2013.01); *A61N 1/36139* (2013.01); *A61N 1/36178* (2013.01); *G16H 20/30* (2018.01); *A61B 5/4082* (2013.01); *A61B 5/7257* (2013.01); *A61N 1/36064* (2013.01); *A61N 1/36071* (2013.01); *A61N 1/36082* (2013.01)

(58) Field of Classification Search
    CPC ................ A61N 1/0534; A61N 1/3606; A61N 1/36067; A61N 1/36139; A61N 1/36178; A61N 1/36064; A61N 1/36071; A61N 1/36082
    USPC .......................................................... 607/45
    See application file for complete search history.

(56) References Cited

U.S. PATENT DOCUMENTS

| | | | |
|---|---|---|---|
| 6,366,813 B1 | 4/2002 | DiLorenzo |
| 6,473,639 B1 | 10/2002 | Fischell et al. |
| 6,480,743 B1 | 11/2002 | Kirkpatrick et al. |
| 6,820,019 B1 | 11/2004 | Kelly et al. |
| 6,873,872 B2 | 3/2005 | Gkuckman et al. |
| 6,993,384 B2 | 1/2006 | Bradley et al. |
| 7,024,247 B2 | 4/2006 | Gliner et al. |
| 7,089,059 B1 | 8/2006 | Pless |
| 7,127,296 B2 | 10/2006 | Bradley |
| 7,177,678 B1 | 2/2007 | Osorio et al. |
| 7,231,254 B2 | 6/2007 | DiLorenzo |
| 7,236,830 B2 | 6/2007 | Gliner |
| 7,277,758 B2 | 10/2007 | DiLorenzo |
| 7,385,443 B1 | 6/2008 | Denison |
| 7,620,456 B2 | 11/2009 | Gliner et al. |
| 7,787,958 B2 | 8/2010 | Stevenson |
| 7,847,628 B2 | 12/2010 | Denison |
| 8,019,419 B1 | 9/2011 | Panescu et al. |
| 8,078,281 B2 | 12/2011 | Priori et al. |
| 8,135,473 B2 | 3/2012 | Miesel et al. |
| 8,190,251 B2 | 5/2012 | Molnar et al. |
| 8,224,452 B2 | 7/2012 | Pless et al. |
| 8,280,514 B2 | 10/2012 | Lozano et al. |
| 8,396,565 B2 | 3/2013 | Singhal et al. |
| 8,423,145 B2 | 4/2013 | Pless et al. |
| 8,473,063 B2 | 6/2013 | Gupta et al. |
| 8,504,154 B2 | 8/2013 | Wanasek |
| 8,521,294 B2 | 8/2013 | Sarma et al. |
| 8,543,221 B2 | 9/2013 | Campbell et al. |
| 8,594,795 B2 | 11/2013 | Tcheng et al. |
| 8,644,930 B2 | 2/2014 | Kelly |
| 8,679,038 B1 | 3/2014 | Giuffrida |
| 8,718,757 B2 | 5/2014 | Bradley et al. |
| 8,744,587 B2 | 6/2014 | Miesel et al. |
| 8,825,175 B2 | 9/2014 | King |
| 8,892,208 B2 | 11/2014 | Flynn et al. |
| 8,942,809 B2 | 1/2015 | Assaf et al. |
| 8,954,152 B2 | 2/2015 | Gupta et al. |
| 8,983,617 B2 | 3/2015 | Chavan et al. |
| 9,002,449 B2 | 4/2015 | Kameli |
| 9,061,140 B2 | 6/2015 | Shi et al. |
| 9,089,704 B2 | 7/2015 | Kelly |
| 9,119,964 B2 | 9/2015 | Marnfeldt |
| 9,192,760 B2 | 11/2015 | Bradley et al. |
| 9,211,417 B2 | 12/2015 | Heldman et al. |
| 9,238,138 B2 | 1/2016 | Lee et al. |
| 9,248,280 B2 | 2/2016 | Moffitt et al. |
| 9,375,582 B2 | 6/2016 | Kaula et al. |
| 9,381,356 B2 | 7/2016 | Parker et al. |
| 9,399,132 B2 | 7/2016 | Parramon et al. |
| 9,421,379 B2 | 8/2016 | Zhu |
| 9,445,730 B2 | 9/2016 | Snyder et al. |
| 9,504,832 B2 | 11/2016 | Libbus et al. |
| 9,521,979 B2 | 12/2016 | Stanslaski et al. |
| 9,522,278 B1 | 12/2016 | Heldman et al. |
| 9,656,089 B2 | 5/2017 | Yip et al. |
| 9,750,938 B2 | 9/2017 | Ternes et al. |
| 9,844,676 B2 | 12/2017 | Zhang et al. |
| 9,888,861 B2 | 2/2018 | Carlson et al. |
| 10,154,812 B2 | 12/2018 | Howard |
| 10,219,697 B2 | 3/2019 | Muller |
| 10,471,259 B2 | 11/2019 | Stanslaski et al. |
| 10,596,379 B2 | 3/2020 | Arlotti et al. |
| 10,639,480 B2 | 5/2020 | Dearden et al. |
| 10,864,368 B2 | 12/2020 | Stanslaski et al. |
| 10,933,243 B2 | 3/2021 | Senderowicz et al. |
| 11,083,402 B2 | 8/2021 | Nelson et al. |
| 11,160,979 B1 | 11/2021 | Giuffrida et al. |
| 11,224,747 B2 | 1/2022 | Bouton et al. |
| 11,318,296 B2 | 5/2022 | Xiao et al. |
| 11,318,309 B2 | 5/2022 | Marceglia et al. |
| 11,679,260 B2 | 6/2023 | Senderowicz et al. |
| 12,064,628 B2 | 8/2024 | Senderowicz et al. |
| 2001/0029391 A1 | 10/2001 | Gluckman et al. |
| 2002/0177882 A1 | 11/2002 | DiLorenzo |
| 2003/0114886 A1 | 6/2003 | Gluckman et al. |
| 2004/0073273 A1 | 4/2004 | Gluckman et al. |
| 2005/0065427 A1 | 3/2005 | Magill et al. |
| 2007/0162086 A1 | 7/2007 | DiLorenzo |
| 2007/0225674 A1 | 9/2007 | Molnar et al. |
| 2008/0183245 A1 | 7/2008 | Van Oort et al. |
| 2008/0269836 A1 | 10/2008 | Foffani et al. |
| 2009/0082829 A1 | 3/2009 | Panken et al. |
| 2009/0099627 A1 | 4/2009 | Molnar et al. |
| 2010/0114237 A1 | 5/2010 | Giftakis et al. |
| 2010/0327887 A1 | 12/2010 | Denison et al. |
| 2011/0015702 A1 | 1/2011 | Ternes et al. |
| 2011/0264165 A1 | 10/2011 | Molnar et al. |
| 2012/0016435 A1 | 1/2012 | Rom |
| 2013/0053722 A1 | 2/2013 | Carlson et al. |
| 2016/0242645 A1 | 8/2016 | Muller |
| 2018/0085572 A1 | 3/2018 | Stanslaski et al. |
| 2019/0269916 A1 | 9/2019 | Senderowicz et al. |
| 2020/0188675 A1 | 6/2020 | Marceglia et al. |
| 2020/0254261 A1 | 8/2020 | Arlotti et al. |
| 2021/0154476 A1 | 5/2021 | Senderowicz et al. |
| 2022/0001181 A1 | 1/2022 | Zylberberg et al. |
| 2022/0016415 A1 | 1/2022 | Arlotti et al. |
| 2022/0323762 A1 | 10/2022 | Marceglia et al. |
| 2023/0285751 A1 | 9/2023 | Senderowicz et al. |

FOREIGN PATENT DOCUMENTS

| | | | |
|---|---|---|---|
| EP | 1 940 508 B1 | 12/2011 | |
| IT | MI-2015A000219 | 2/2016 | |
| JP | 2005-252497 A | 9/2005 | |
| JP | 2009-033303 A | 2/2009 | |
| JP | 2010-517471 A | 5/2010 | |
| JP | 2010-517472 A | 5/2010 | |
| WO | WO-00/07494 A2 | 2/2000 | |
| WO | WO-00/07494 A3 | 2/2000 | |
| WO | WO-2007/049105 A1 | 5/2007 | |
| WO | WO-2013/123112 A1 | 8/2013 | |
| WO | WO-2014116850 A1 * | 7/2014 | ........... A61N 1/0534 |
| WO | WO-2015/069797 A1 | 5/2015 | |
| WO | WO-2016/132258 A1 | 8/2016 | |
| WO | WO-2018/017463 A1 | 1/2018 | |
| WO | WO-2018/064193 A1 | 4/2018 | |
| WO | WO-2018/064225 A1 | 4/2018 | |
| WO | WO-2018/112164 A1 | 6/2018 | |
| WO | WO-2018/160271 A1 | 9/2018 | |

(56) References Cited

FOREIGN PATENT DOCUMENTS

| WO | WO-2018/187080 A1 | 10/2018 |
|---|---|---|
| WO | WO-2019/073341 A1 | 4/2019 |
| WO | WO-2019/153094 A1 | 8/2019 |
| WO | WO-2020/086119 A1 | 4/2020 |
| WO | WO-2020/087135 A1 | 5/2020 |
| WO | WO-2021/127379 A1 | 6/2021 |
| WO | WO-2021/138543 A1 | 7/2021 |
| WO | WO-2021/141814 A1 | 7/2021 |
| WO | WO-2021/167946 A1 | 8/2021 |
| WO | WO-2022/029445 A1 | 2/2022 |

OTHER PUBLICATIONS

BioWorld MedTech (2018). UCSF Using Closed Loop Adaptive DBS, Clarivate Analytics, 24 total pages.

Bronstein, J.M. et al. (2011). "Deep Brain Stimulation For Parkinson Disease," Archives of Neurology 68:165-171.

Brown, P. et al. (2005). "Basal Ganglia Local Field Potential Activity: Character and Functional Significance in the Human," Clinical Neurophysiology 116:2510-2519.

Brown, P. et al. (2001). "Dopamine Dependency of Oscillations Between Subthalamic Nucleus and Palladium in Parkinson's Disease," J. Neurosci. 21:1033-1038.

Brown, P. (2003). "Oscillatory Nature of Human Basal Ganglia Activity; Relationship to the Pathophysiology of Parkinson's Disease," Mov. Disord. 18:357-363.

Burgess, J.G. et al. (2010). "Identifying Tremor-Related Characteristics Of Basal Ganglia Nuclei During Movement In The Parkinsonian Patient," Parkinsonism & Related Disorders 16:671-675.

Cassidy, M. et al. (2002). "Movement-Related Changes in Synchronization in the Human Basal Ganglia," Brain 125:1235-1246.

Chang, S.Y. et al. (2013). "Development Of The Mayo Investigational Neuromodulation Control System: Toward A Closed-Loop Electrochemical Feedback System For Deep Brain Stimulation," Journal of Neurosurgery 119:1556-1565.

Cogan, S.F. (2008). "Neural stimulation and recording electrodes," Annu Rev Biomed Eng. 10:275-309.

de Hemptinne, C. et al. (2015). "Therapeutic Deep Brain Stimulation Reduces Cortical Phase-Amplitude Coupling In Parkinson's Disease," Nature Neuroscience 18:779-786.

Denison, T. et al. (2007). "A 2 µW 100 nV/rtHz chopper-stabilized instrumentation amplifier for chronic measurement of neural filed potentials," IEEE J. of Solid-State Circuits 42:2934-2945.

Doyle, L.M.F. et al. (2005). "Levodopa-Induced Modulation of Subthalamic Beta Oscillations During Self-Paced Movements in Patients With Parkinson's Disease," Eur. J. Neurosci. 21:1403-1412.

Eusebio, A et al. (2011). "Deep Brain Stimulation Can Suppress Pathological Synchronisation In Parkinsonian Patients," J. of Neurol. Neurosurgery & Psychiatry 82:569-573.

Foffani, G. et al. (2003). "300-HZ Subthalamic Oscillations in Parkinson's Disease," Brain 126:2153-2163.

Foffani, G. et al. (2004). "Adaptive Autoregressive Identification With Spectral Power Decomposition for Studying Movement-Related Activity in Scalp EEG Signals and Basal Ganglia Local Field Potentials," J. Neural Eng. 1:165-173.

Foffani, G. et al. (2005). "Physiological Recordings From Electrodes Implanted in the Basal Ganglia for Deep Brain Stimulation in Parkinson's Disease. The Relevance of Fast Subthalamic Rhythms," Acta Neurochir. Suppl. 93:97-99.

Foffani, G. et al. (2005). "Altered Subthalamo-Pallidal Synchronisation in Parkinsonian Dyskinesias," J. Neural Neurosurg. Psychiatry 76:426-428.

Foffani, G. et al. (2005). "Movement-Related Frequency Modulation of Beta Oscillatory Activity in the Human Subthalamic Nucleus," J. Physiol. 568:699-711.

Fogelson, N. et al. (2005). "Reciprocal Interactions Between Oscillatory Activi-ties of Different Frequencies in the Subthalamic Region of Patients With Parkinson's Disease," Eur. J. Neurosci. 22:257-266.

Hamani, C. et al. (2005). "Bilateral subthalamic nucleus stimulation for Parkinson's disease: A systematic review of the clinical literature," Neurosurgery 56:1313-1321.

International Search Report mailed on May 16, 2019, for PCT Application No. PCT/IB2019/051428, filed on Feb. 21, 2019, 3 pages.

International Search Report mailed on May 18, 2016, for PCT Application No. PCT/IB2016/050735, filed on Feb. 11, 2016, 7 pages.

Kuhn, A.A. et al. (2009). "Pathological Synchronisation In The Subthalamic Nucleus Of Patients With Parkinson's Disease Relates To Both Bradykinesia And Rigidity," Exp. Neurology 215:380-387.

Kühn, A.A. et al. (2005). "The Relationship Between Local Field Potential and Neuronal Discharge in the Subthalamic Nucleus of Patients With Parkinson's Disease," Experimental Neurology 194:212-220.

Kühn, A.A. et al. (2004). "Event-Related Beta Desynchronization in Human Subthalamic Nucleus Correlates With Motor Performance," Brain 127:735-746.

Levy, R. et al. (2002). "Dependence of Subthalamic Nucleus Oscillations on Movement and Dopamine in Parkinson's Disease," Brain 125:1196-1209.

Limousin, P. et al. (1996). "Abnormal Involuntary Movements Induced By Subthalamic Nucleus Stimulation In Parkinsonian Patients," Movement Disorders 11:231-235.

Modolo, J. et al. (2010). "Past, present and future of bran stimulation," Mathematical modelling of Natural Phenomena 5:185-207.

Modolo, J. et al. (2010). "Model-driven therapeutic treatment of neurological disorders: Reshaping brain rhythms with neuromodulation," Interface Focus 1:61-74.

Moro, E. et al. (2006). "Subthalamic Nucleus Stimulation: Improvements In Outcome With Reprogramming," Archives of Neurol. 63:1266-1272.

Notice of Allowance mailed on Nov. 14, 2019, for U.S. Appl. No. 15/550,284, filed Aug. 10, 2017, 7 pages.

Notice of Allowance mailed on Jun. 17, 2020, for U.S. Appl. No. 16/282,167, filed Feb. 21, 2019, 8 pages.

Pedram, A. et al. (2013). "A translational platform for prototyping closed-loop neuromodulation systems," Frontiers in Neural Circuits 6:117.

Priori, A et al. (2004). "Rhythm-Specific Pharmacological Modulation Of Subthalamic Activity In Parkinson's Disease," Experimental Neurology 189:369-379.

Priori, A et al. (2013). "Adaptive Deep Brain Stimulation (aDBS) Controlled By Local Field Potential Oscillations," Experimental Neurology 245:77-86.

Priori, et al, "Movement-Related Modulation of Neural Activity in Human Basal Ganglia and its L-Dopa Dependency: Recordings From Deep Brain Stimulation Electrodes in Patients With Parkinson's Disease", Neurol. Sci., Sep. 2002, pp. S101-S102.

Qian, X. et al. (2017). "A Method for Removal of Deep Brain Stimulation Artifact from Local Field Potentials," IEEE Trans. on Neural Systems and Rehabilitation Engineering, 25(12), 2217-2226.

Rosin, B. et al. (2011). "Closed-Loop Deep Brain Stimulation Is Superior in Ameliorating Parkinsonism," Neuron 72:370-384.

Santaniello, S. et al. (2011). "Closed-Loop Control Of Deep Brain Stimulation: A Simulation Study," IEEE Transactions on Neural Systems and Rehabilitation Engineering 19:15-24.

Silberstein, P. et al. (2003). "Patterning of Globus Pallidus Local Field Poten-tials Differs Between Parkinson's Disease and Dystonia," Brain 126:2597-2608.

Stanslaski, S. et al. (2011). "Design and validation of a fully implantable, chronic, closed-loop neuromodulation device with concurrent sensing and stimulation," IEEE Trans Neural Syst Rehabil Eng. 20:410-421.

Williams, D. et al. (2002). "Dopamine-Dependent Changes in the Functional Connectivity Between Basal Ganglia and Cerebral Cortex in Humans," Brain 125:1558-1569.

Written Opinion of the International Searching Authority mailed on May 16, 2019, for PCT Application No. PCT/IB2019/051428, filed on Feb. 21, 2019, 5 pages.

(56) References Cited

OTHER PUBLICATIONS

Written Opinion of the International Searching Authority mailed on May 18, 2016, for PCT Application No. PCT/IB2016/050735, filed on Feb. 11, 2016, 8 pages.

Yoshida, F. et al. (2010). "Value Of Subthalamic Nucleus Local Field Potentials Recordings In Predicting Stimulation Parameters For Deep Brain Stimulation In Parkinson's Disease," Journal of Neurology, Neurosurgery & Psychiatry 81:885-889.

Zhou, A. et al. (2019). "A wireless and artefact-free 128-channel neuromodulation device for closed-loop stimulation and recording in non-human primates," Nature Biomedical Engin. 3:15-26.

Zhou, A. et al. (2017). WAND: A 128-channel, closed-loop, wireless artifact-free neuromodulation device, 30 total pages.

Gui Yun et al. (Oct. 2013). "A multi-channel fully differential programmable integrated circuit for neural recording application," J. Semicond. 34:105009-1-8.

International Search Report mailed on Jan. 28, 2022, for PCT Application No. PCT/IB2021/056435, filed on Jul. 16, 2021, 6 pages.

Kuncel, A.M. et al. (2004). "Selection of stimulus parameters for deep brain stimulation," Clin. Neurophysiol. 115:2431-2441.

Lin, Y.P. et al. (2016). "A Battery-Less, Implantable Neuro-Electronic Interface for Studying the Mechanisms of Deep Brain Stimulation in Rat Models," IEEE Trans. Biomed. Circuits Syst. 10:98-112.

Non-Final Office Action mailed on May 18, 2022, for U.S. Appl. No. 17/165,124, filed Feb. 2, 2021, 9 pages.

Notice of Allowance mailed on Dec. 17, 2021, for U.S. Appl. No. 16/706,552, filed Dec. 6, 2019, 8 pages.

Notice of Allowance mailed on Oct. 31, 2022, for U.S. Appl. No. 17/165,124, filed Feb. 2, 2021, 9 pages.

Notice of Allowance mailed on Feb. 21, 2023, for U.S. Appl. No. 17/165,124, filed Feb. 2, 2021, 9 pages.

Written Opinion of the International Searching Authority mailed on Jan. 28, 2022, for PCT Application No. PCT/IB2021/056435, filed on Jul. 16, 2021, 13 pages.

Zhao-Hui, W. et al. (2015). "Implantable analog front-end with high PSRR and CMRR for neural signal acquisition," Journal of South China University of Technology (Natural Science Edition) 43:15-20 (English Abstract Provided).

Non-Final Office Action mailed on Dec. 21, 2023, for U.S. Appl. No. 18/320,100, filed May 18, 2023, 12 pages.

Notice of Allowance mailed on Apr. 15, 2024, for U.S. Appl. No. 18/320,100, filed May 18, 2023, 8 pages.

Extended European Search Report mailed on Dec. 14, 2020, for EP Application No. 20 196584.5, filed on Feb. 11, 2016, 9 pages.

Mukherjee, R. et al. (Dec. 2017). "Prediction of disorder of brain using EEG signal processing in MATLAB GUI platform," Proceedings of the 2nd International Conference on Electrical & Electronic Engineering (ICEEE), 4 pages.

Non-Final Office Action mailed on Aug. 2, 2024, for U.S. Appl. No. 17/378,033, filed Jul. 16, 2021, 18 pages.

Non-Final Office Action mailed on Aug. 19, 2024, for U.S. Appl. No. 17/706,378, filed Mar. 28, 2022, 13 pages.

Sakkalis, V. et al. (2008). "Parametric and nonparametric EEG analysis for the evaluation of EEG activity in young children with controlled epilepsy," Comput. Intell. Neurosci., vol. 2008, Article ID 462593, 15 pages.

\* cited by examiner

APPARATUS AND METHOD FOR TREATING NEUROLOGICAL DISORDERS

The present invention concerns an apparatus and a method for treating neurological disorders. In greater detail, the present invention concerns an apparatus and a method for treating neurological disorders based on the feedback of deep brain stimulation, therefore capable of detecting biopotentials from a stimulation electrode or from neighbouring electrodes, correlating such signals with the clinical state of the patient and feeding the stimulation parameters back in order to optimise the therapy.

In the present description and in the subsequent claims, the expression "local biopotentials" means the electric potentials produced by groups of neurones close to the recording and stimulation electrodes.

In the present description and in the subsequent claims, the expression "local field potentials" means the sum of the pre and post synaptic activity around a stimulation electrode implanted in the brain.

In the present description and in the subsequent claims, the expression "base clinical state" of a patient means the state of the patient in the absence of therapies, both pharmacological and by stimulation, for a sufficiently long time period, so that the effects of the therapies have totally worn off, in general equal to at least 12 hours.

As known, deep brain stimulation, also known by the acronym DBS, is a therapeutic method based on the modulation of the activities of structures of the central nervous system through an electric stimulation delivered locally. For this purpose, electrodes are implanted by neurosurgery. Electric stimulation consists of delivering a train of electric pulses in the brain area of interest through the implanted electrode, which for this purpose is connected to a pulse generator.

Deep brain stimulation is currently used in clinical trials or for the treatment of epilepsy, migraines, some psychiatric disturbances, pain and movement disorders, such as dystonia, tremor and Parkinson's disease. Such a method allows the functional autonomy of patients to be improved, thus offering an improved quality of life. Since the use of deep brain stimulation is particularly consolidated in the treatment of Parkinson's disease, in the present description reference will mainly be made, although only as an example and not for limiting purposes, to such a disease.

In the case of Parkinson's disease, the implantation areas of the electrode most used in clinical practice are some structures of the grey nucleus, including in particular the internal globus pallidus and the subthalamic nucleus, as well as the inner peduncle pontine nucleus. The choice of the implantation area is at the discretion of the neurologist based on the symptoms to be tackled. As an example, it should be considered, indeed, that Parkinson's disease is characterised by a wide spectrum of motor and non-motor symptoms, where the motor symptoms comprise, amongst other things, rigidity, bradykinesia, rest tremor, akinesia, postural instability, inability to walk and so on. Clinical studies widely support the benefits brought by deep brain stimulation at the subthalamic nucleus, which is therefore the preferred implantation area in most treatments. Such a treatment method can cause various side effects including dyskinesia, language and psychiatric difficulties that can, nevertheless, be mitigated through a reprogramming of the stimulation parameters.

In the case of conventional brain stimulation, the parameter setting process is carried out empirically, requiring time, clinical experience and numerous visits to adjust to the optimal values. Moreover, such adjustment leads to setting that, even if initially optimal, is unable to adapt to variations that came afterwards. Indeed, once the parameters have been set, the stimulation is delivered independently from the clinical state of the patient, not being able to adapt to possible variations of such a clinical state. Therefore, clinical fluctuations characterising an advanced stage of Parkinson's disease remain uncontrolled.

In order to overcome the limitations described above, an apparatus for treating neurological disorders has been made that is capable of monitoring the clinical state of the patient by recording a physiological marker, also known as biomarker, as control variable, and of adapting the stimulation parameters to the clinical state detected. Such a system is known as adaptive brain stimulation. An example of such an apparatus is described in European patent EP 1 940 508. Through such an apparatus it is possible to decrease the time necessary to set the optimal parameters and decrease the occurrence of side effects.

From EP 1 940 508 it is known to use the local field potentials as a marker based on which to adapt the stimulation parameters. The local field potentials prove particularly suitable for the purpose, since they correlate with both motor and non-motor symptoms, they can be recorded by the stimulation electrode even during the stimulation itself, they can be influenced through stimulation and maintain such properties for a long time after the electrode has been implanted. Neurophysiological recordings carried out through an electrode for deep brain stimulation have, indeed, shown that the local field potentials are correlated to the clinical state of the patient, for example to the performance of movements, as well as to cognitive and behavioural stimuli.

In relation to the correlation between the local field potentials and the symptoms of the disorders to be treated, the Applicant has observed that a lot of the information content of the local field potentials relative to the disorders to be treated can be extrapolated through frequency analysis. In other words, the Applicant has found that there is a link between the power of the local field potentials in certain frequency bands and specific symptoms of the disturbance to be treated. Specifically, the Applicant has identified a relationship between sets of power values of the local field potentials and the variations in the clinical state in terms of symptoms to be treated. In particular, the significant oscillatory rhythms in terms of their correlation with the symptomatic state of the patient are: low frequencies (4-10 Hz), the beta band (alpha/low beta: 11-20 Hz, high beta: 20-35 Hz), the gamma band (60-80 Hz) and high frequencies (250-350 Hz).

In line with such an observation, patent EP 2 004 036 also describes a medical device that, for the treatment of a motor disorder, uses a physiological marker of the clinical state of a patient. In particular, the physiological marker is calculated based on two values representative of the amount of oscillatory activity of the physiological signal detected, each relative to a different range of frequencies. Patent EP 2 004 036 also refers to the possibility of adjusting the therapy in feedback based on the two values representative of the amount of oscillatory activity, in particular by adjusting the stimulation parameters so as to keep the biomarker calculated based on such two values, in a predetermined range. EP 2 004 036 does not, however, provide any indication concerning the adjustment logic for an optimal adaptation of the stimulation parameters.

Also known is the study of Santaniello et al. Described in the article titled "Closed-Loop Control of Deep Brain Stimulation: A Simulation Study" published in IEEE Transactions on neural systems and rehabilitation engineering, Vol. 19, No. 1, February 2011, pages 15-24, which has the purpose of developing a closed-loop control system for automatically adjusting the stimulation parameters based on the neuronal signals recorded through the same stimulation electrode, in particular based on the local field potentials. Such a control system comprises, downstream of the transfer function, a saturating trend function that limits the amplitude of the stimulation parameters if the transfer function determines an output value outside a predetermined range. Such a limitation is therefore carried out as a function of the output of the transfer function.

However, such a system is unable to correlate the power of the local field potentials calculated in specific frequency bands with the stimulation parameters, so as to take into account the link observed by the Applicant between the particular sets of band power values and the specific symptoms of the disturbance to be treated. In other words, the transfer function of the control system described in Santaniello applies the same law of variability independently from the set to which the power value that it receives in input belongs.

In light of the above, the Applicant has found the need to devise an apparatus and a method capable of administering a deep brain stimulation therapy in an optimised manner as a function of the instantaneous clinical state of the patient, expressed through a physiological marker calculated from the local field potentials measured on the patient.

The problem forming the basis of the present invention is therefore that of making an apparatus and a method for treating neurological disorders that is able to adapt the stimulation administered in an optimal manner as a function of the instantaneous clinical state of the patient, operating automatically and continuously.

For this purpose, the Applicant has perceived the need to identify a law of variability that correlates the stimulation parameters with the local field potentials, based on which it is possible to construct an automatic control of the therapy that adapts in an optimised and quick manner to possible changes in the clinical state of the patient.

In accordance with a first aspect thereof, the invention concerns an apparatus for treating neurological disorders comprising at least one electrode implantable in the brain of a patient and a processing and stimulation device connected to the at least one electrode, wherein the processing and stimulation device comprises at least one stimulation module adapted to generate a stimulation signal to be sent to the at least one electrode, the stimulation signal being characterised by a plurality of parameters, at least one acquisition module of a signal characteristic of cerebral activity coming from the brain of the patient, adapted to determine its power in at least one frequency band, and at least one control module of at least one parameter of the stimulation signal as a function of the power of the acquired signal characteristic of cerebral activity based on a transfer function having a saturating trend, wherein the transfer function is such as to set said at least one parameter ($V_a$, $V_d$, $V_f$) of the stimulation signal ($V_{stim}$) differently dependent on a plurality of power ranges, keeping it within a predetermined stimulation range ($[V_{i\_HighThreshold}; V_{i\_LowThreshold}]$) with i=a,d,f. In the present description and in the subsequent claims, the expression "transfer function having a saturating trend" means a function that for input values greater than or less than respective first and second predetermined input values respectively places the output variable (different from the input variable) equal to a first and a second predetermined output value and for input values comprised between the first and the second predetermined input values, the output can take values based on a predetermined law of variability. Therefore, in the present description and in the subsequent claims, the definition of "saturating trend function" should not be taken in the narrow sense as a function that forces the input variable to not take values in output greater or less than predetermined thresholds.

The Applicant has observed that, for example, the oscillations in the beta band are suppressed following administration of a suitable drug (for example dopamine) and correlate with the preparation and performance of the movement. Such oscillations reflect the response of the grey nucleus to the drug and correlate with the motor state. In the same way, it has been demonstrated that a deep brain stimulation treatment induces a power reduction in the beta band.

In other words, when an improvement of the motor state of the patient is observed after the administration of the drug or after a deep brain stimulation therapy, a corresponding percentage reduction of the power of the local field potentials calculated in the beta band with respect to the base clinical state, i.e. the clinical state prior to the administration of therapies, is observed. The variation of the motor state of the patient is expressed in UPDRS (Unified Parkinson's Disease rating scale) as percentage values with respect to the base state.

Similarly, the Applicant has observed that the oscillations in the band of low frequencies (4-10 Hz) increases with a deep brain stimulation and/or pharmacological treatment. In other words, when a percentage decrease in the UPDRS scale is observed, i.e. an improvement in the clinical state of the patient after administration of the drug or the deep stimulation therapy, a corresponding increase in the power of the local field potentials calculated in the band of low frequencies with respect to the base clinical state is observed.

The Applicant therefore started from the assumption that an improvement in the clinical state of the patient is correlated to a percentage variation of the power of the local field potentials, and hypothesised a proportional relationship between such a power calculated in a certain frequency band, whether it is calculated in the frequency domain, or in the time domain, and the clinical state, for example expressed in UPDRS scale.

The Applicant has also hypothesised that the relationship between stimulation and local field potentials can be expressed through a proportional relationship between the stimulation signal and the power of the local field potentials. From such an assumption it follows that the clinical state can be expressed as a function of the stimulation signal.

In accordance with the assumptions outlined above it is possible to control the clinical state of the patient by modifying the stimulation parameters as a function of the power in a certain frequency band according to the mathematical function indicated above.

Such a function determines that, for certain ranges of input power values, the stimulation parameters can vary as a function of the input power, adapting to the instantaneous clinical state of the patient and for other ranges of input power values the stimulation parameters are set equal to respective saturation values at which the stimulation was still actually effective. In this way, the occurrence of side effects due to stimulation therapy is avoided, at the same time ensuring a definite benefit induced by the stimulation.

Similarly, in accordance with a second aspect thereof, the invention concerns a method for treating neurological disorders comprising the steps consisting of:
- sending at least one stimulation signal characterised by a plurality of parameters to at least one electrode implantable in the brain of a patient;
- acquiring at least one signal characteristic of cerebral activity coming from the brain of the patient and determining its power in at least one frequency band; and
- adjusting at least one parameter of the stimulation signal as a function of the power of the acquired signal characteristic of cerebral activity based on a transfer function having a saturating trend, wherein the transfer function is such as to set said at least one parameter ($V_a$, $V_d$, $V_f$) of the stimulation signal ($V_{stim}$) differently dependent on a plurality of power ranges, keeping it within a predetermined stimulation range ([$V_{i\_HighThreshold}$; $V_{i\_LowThreshold}$]) with i=a,d,f.

Advantageously, the method for treating neurological disorders according to the invention achieves the technical effects described above in relation to the apparatus.

The present invention, in at least one of the aforementioned aspects, can have at least one of the following preferred characteristics, which are in particular able to be combined with each other as desired in order to satisfy specific application requirements.

Preferably, the transfer function having a saturating trend as a function of a plurality of power ranges is a piecewise function, placing the stimulation parameter equal to a first value of the stimulation parameter for powers of the acquired signal greater than a first power limit value and placing the stimulation parameter equal to a second value of the stimulation parameter for powers of the acquired signal below a second power limit value according to the following law of variability:

$$sat(U(P_{BF})) = \begin{cases} V_{i2} & \text{for } P_{BF} \geq P_{BF2} \\ U_i(P_{BF}) & \text{for } P_{BF2} > P_{BF} > P_{BF1} \\ V_{i1} & \text{for } P_{BF} \leq P_{BF1} \end{cases}$$

with $V_{i1}$ and $V_{i2}$ alternatively respectively placed equal to the minimum value $V_{i\_LowThreshold}$ and to the maximum value $V_{i\_HighThreshold}$, $P_{GF2}$ and $P_{BF1}$ equal, respectively, to a maximum limit value and a minimum limit value of the saturation ranges of the stimulation parameter $V_i$ and $U_i(P_{BF})$ being a law of variability $U_i(P_{BF})$ of the stimulation parameter $V_i$ outside of the saturation ranges. More preferably, the law of variability $U_i(P_{BF})$ of the stimulation parameter outside of the saturation ranges is of the following type:

$$U_i(P_{BF}) = K_{1i} \frac{V_{i2} - V_{i1}}{P_{BF2} - P_{BF1}}(P_{BF} - P_{BF1}) + V_{i1}.$$

Even more preferably, the law of variability $U_i(P_{BF})$ of the stimulation parameter $V_i$ outside of the saturation ranges comprises a further additional term ($K_{2i}$), thereby resulting in:

$$U_i(P_{BF}) = K_{1i} \frac{V_{i2} - V_{i1}}{P_{BF2} - P_{BF1}}(P_{BF} - P_{BF1}) + V_{i1} + K_{2i}.$$

Alternatively, the law of variability $U_i(P_{BF})$ of the stimulation parameter outside of the saturation ranges is of the following type:

$$U_i(P_{BF}) = K_{1i}(V_{i2} - V_{i1}) * \left(\frac{1}{1 + e^{-p\left(P_{BF} - \frac{P_{BF2} - P_{BF1}}{2}\right)}}\right) + V_{i1}.$$

More preferably, the law of variability $U_i(P_{BF})$ of the stimulation parameter $V_i$ outside of the saturation ranges comprises a further additional term ($K_{2i}$), thereby resulting in:

$$U_i(P_{BF}) = K_{1i}(V_{i2} - V_{i1}) * \left(\frac{1}{1 + e^{-p\left(P_{BF} - \frac{P_{BF2} - P_{BF1}}{2}\right)}}\right) + V_{i1} + K_{2i}.$$

Advantageously, the selected laws of variability in feedback allow a vast range of adjustment strategies to be carried out through a suitable calibration of the parameters thereof. This flexibility is an essential requirement that allows the use of the apparatus according to the present invention in association with multiple different neurological disorders, each characterised by mutually heterogeneous symptoms that in turn correlate with the local field potentials in different frequency bands and with different time dynamics.

Preferably, the at least one acquisition module comprises processing means for transforming the acquired signal characteristic of cerebral activity in the frequency domain.

In an even more preferred manner, the processing means for transforming the acquired signal characteristic of cerebral activity in the frequency domain implement a Fourier transform, preferably of the FFT (Fast Fourier Transform) type.

More preferably, the processing means for transforming the acquired signal characteristic of cerebral activity in the frequency domain are of the hardware or software type.

Preferably, the at least one acquisition module comprises an integral block for conditioning the acquired signal characteristic of cerebral activity.

Alternatively or in combination, the at least one acquisition module comprises a derivative block for conditioning the acquired signal characteristic of cerebral activity.

In this way, advantageously, it is possible to carry out prior conditioning of the signal fed to the control module that is independent and specific for each stimulation parameter.

Preferably, the at least one stimulation module is a pulse generator.

Preferably, the at least one control module is suitable for implementing the above law of variability $U_i(P_{BF})$.

Preferably, the frequency band BF and the parameters of the law of variability, such as a first $V_{i1}$ and a second $V_{i2}$ threshold value of a stimulation parameter $V_i$, a maximum power value $P_{BF2}$ and a minimum power value $P_{BF1}$ are obtained according to the following steps:

a) Identifying at least one maximum threshold value $V_{i\_HighThreshold}$ of a stimulation parameter $V_i$ above which the patient shows signs of side effects caused by the stimulation and a minimum threshold value $V_{i\_LowThreshold}$ for which the patient shows the minimum or zero benefit induced by stimulation, and placing the extremes of the predetermined stimulation range ($[V_{i2}; V_{i1}]$) alternatively respectively equal to the maximum threshold value $V_{i\_HighThreshold}$ and minimum threshold value $V_{i\_LowThreshold}$ of the stimulation parameter or to a percentage thereof;

b) Determining the frequency band BF, detecting a frequency peak of the power spectrum of a signal characteristic of cerebral activity of the patient recorded in the absence of stimulation, the frequency band BF being centred on such a frequency peak and having a bandwidth selected arbitrarily;

c) Recording the trend over time of the power $P_{BF}$ of a signal characteristic of cerebral activity calculated in the frequency band BF in the three conditions:

base state;

active stimulation at the maximum threshold value $V_{i\_HighThreshold}$ of the stimulation parameter $V_i$ and pharmacological therapy absent; and active stimulation at the maximum threshold value $V_{i\_HighThreshold}$ of the stimulation parameter $V_i$ and pharmacological therapy administered and active;

d) Identifying a maximum power value $P_{BF2}$ and a minimum power value $P_{BF1}$ of the trend recorded at step c).

Preferably, the stimulation signal comprises a train of pulses and the stimulation parameter $V_i$ is chosen from the group consisting of:

The amplitude of the stimulation pulses;

The stimulation pulse repetition frequency;

The stimulation pulse duration.

Preferably, the maximum power value $P_{BF2}$ of the signal characteristic of cerebral activity calculated in the frequency band BF corresponds to the power value $P_{OFFOFF}$ that can be determined when the patient is in the base state and the minimum power value $P_{BF1}$ corresponds to the power value $P_{ONON}$ that can be determined when the patient is subjected both to pharmacological therapy and to stimulation therapy active at the maximum threshold value $V_{i\_HighThreshold}$ of the stimulation parameter.

More preferably, the frequency band BF is a sub-band of the beta band (10-35 Hz).

Alternatively, the minimum power value $P_{BF1}$ of the signal characteristic of cerebral activity calculated in the frequency band BF corresponds to the power value $P_{OFFOFF}$ that can be determined when the patient is in the base state and the maximum power value $P_{BF2}$ corresponds to the power value $P_{ONON}$ that can be determined when the patient is subjected both to pharmacological therapy and to stimulation therapy active at the maximum threshold stimulation parameter $V_{i\_HighThreshold}$. Preferably, in this case, the frequency band BF is a sub-band of the low frequencies (4-10 Hz). Preferably, the signal characteristic of cerebral activity is a signal coming from the grey nucleus. Preferably, the power calculated in at least one frequency band of the acquired signal characteristic of cerebral activity is compared with a reference value and, based on the difference between the calculated power and the reference value, a control signal for a stimulation module is generated that sets the stimulation parameters.

Preferably, the power $P_{BF}$ of the acquired signal characteristic of cerebral activity is integrated with a time constant $\tau$.

Advantageously, the time constant $\tau$ is selected as a function of the adjustment that is wished to be obtained: the greater the time constant $\tau$, the greater the accuracy of the adjustment but also the delay in response of the system. Therefore, the time constant $\tau$ with which the power of band $P_{BF}$ is integrated is chosen seeking the ideal compromise between accuracy and speed of response of the adjustment.

Alternatively or in addition, the power P of the acquired signal characteristic of cerebral activity is a derivative.

Further characteristics and advantages of the present invention will become clearer from the following detailed description of some preferred embodiments thereof, made with reference to the attached drawings.

The different characteristics in the single configurations can be combined with each other as desired according to the previous description, if it were necessary to have advantages resulting specifically from a particular combination.

In such drawings.

In the following description, to illustrate the figures identical reference numerals or symbols are used to indicate constructive elements with the same function. Moreover, for the sake of clarity of illustration, some references are not repeated in all of the figures.

Figure 1:
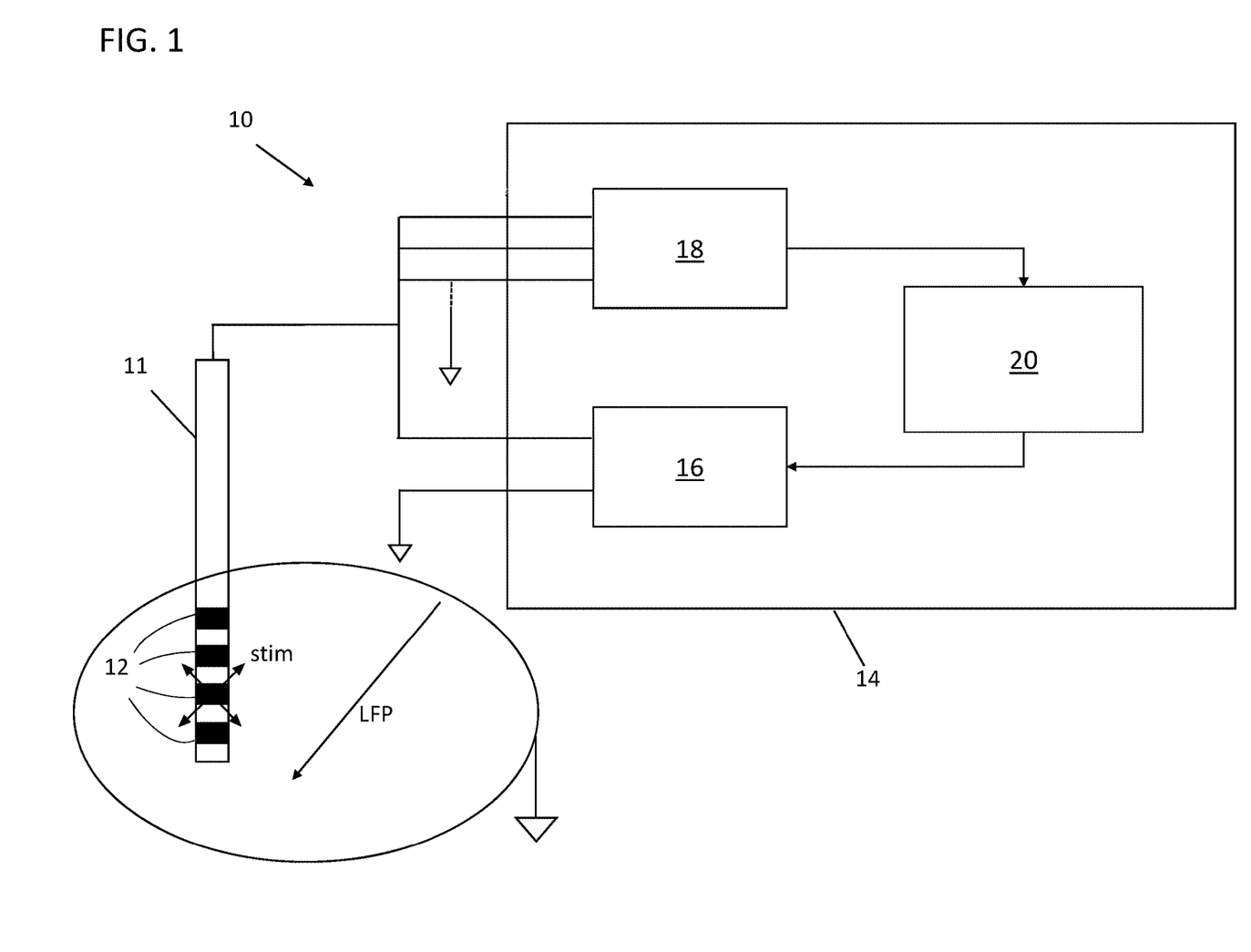
FIG. 1 is a schematic representation of an apparatus for treating neurological disorders according to a preferred embodiment of the present invention.

With reference to FIG. 1, an apparatus for treating neurological disorders is shown, wholly indicated with 10.

The apparatus for treating neurological disorders 10 comprises at least one electro-catheter 11 suitable for being implanted in the brain of a patient to administer an electric stimulation. The electro-catheter 11 preferably comprises at least three metallic contacts accessible through external connections also called electrodes 12. However, it is obviously possible to hypothesise alternative solutions in which the electrodes are not necessarily carried by one same electro-catheter.

The electrodes 12 are connected to a processing and stimulation device 14 that, in the embodiment illustrated in FIG. 1, comprises three functional modules connected together in feedback and interoperating: a stimulation module 16, an acquisition module 18 and a control module 20.

The stimulation module 16 is adapted to generate a stimulation signal $V_{stim}$, characterised by a set of parameters $V_a$, $V_d$, $V_f$, and to send to the electrodes 12 the stimulation signal generated. In particular, the stimulation module 16 is a generator of pulses defined by the amplitude, frequency and duration of the pulses.

The acquisition module 18 is assigned to the acquisition of a signal characteristic of cerebral activity coming from the brain of the patient. In detail, the acquisition module 18 comprises processing means for transforming the acquired signal characteristic of cerebral activity in the frequency domain. Specifically, the processing means carry out an FFT (Fast Fourier Transform) and can be made through hardware means and/or software means. The acquisition module 18 also preferably comprises an integral block and a derivative block (not illustrated) of the signal characteristic of cerebral activity transformed in the frequency domain.

The control module 20 implements an adjuster, preferably a feedback controller. As illustrated more clearly in FIG. 3, the control module 20 is functionally connected, upstream, to the acquisition module 18 and, downstream, to the stimulation module 16 that determines the stimulation signal $V_{stim}$. As a function of the spectral power of the signal characteristic of cerebral activity acquired by the acquisition module 18, the control module 20 determines at least one signal based on which at least one parameter $V_a$, $V_d$, $V_f$ of the stimulation signal $V_{stim}$ set by the stimulation module 16 is defined.

Figure 3:
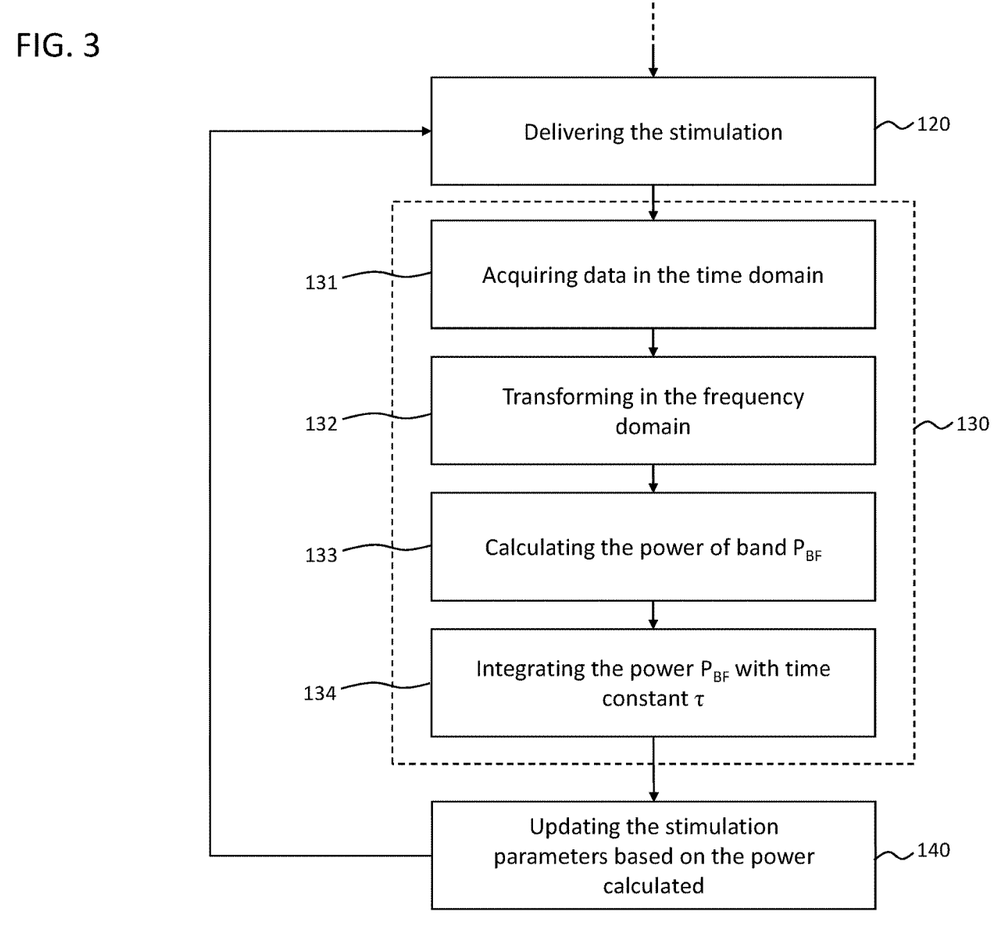
FIG. 3 is a detailed block diagram of a step of the method for treating neurological disorders according to the present invention.

Advantageously, the control module 20 receives in input the signal acquired in the time domain or transformed in the frequency domain by the acquisition module 18 to determine its power. Based on such a power, preferably integrated based on a time constant $\tau$ and/or derived according to specificities of the stimulation parameter to be adjusted, the stimulation parameters are calculated based on a transfer function having a saturating trend such as to also determine that the stimulation parameters are variable between two saturation values ($V_{i\_HighThreshold}$; $V_{i\_LowThreshold}$) between which the stimulation is actually effective.

In particular, the transfer function having a saturating trend is implemented as a piecewise function based on ranges of values of the input power, i.e. such as to place the stimulation parameter $V_i$ equal to a maximum value $V_{i\_HighThreshold}$ or to a minimum value $V_{i\_LowThreshold}$ in the saturation ranges, allowing the stimulation parameter $V_i$ to vary, outside the saturation ranges, as a function of the power $P_{BF}$ of the signal acquired according to a law of variability $U_i(P_{BF})$.

This translates into the following transfer function, where the saturation ranges correspond to powers $P_{BF}$ of the acquired signal greater than a first power limit value $P_{GF2}$ or powers $P_{BF}$ of the acquired signal below a second power limit value $P_{BF1}$:

$$sat(U(P_{BF})) = \begin{cases} V_{i2} & \text{for } P_{BF} \geq P_{BF2} \\ U_i(P_{BF}) & \text{for } P_{BF2} > P_{BF} > P_{BF1} \\ V_{i1} & \text{for } P_{BF} \leq P_{BF1} \end{cases}$$

In particular, the law of variability $U_i(P_{BF})$ of the stimulation parameter outside the saturation ranges is of the following type:

$$U_i(P_{BF}) = K_{1i}\frac{V_{i2} - V_{i1}}{P_{BF2} - P_{BF1}}(P_{BF} - P_{BF1}) + V_{i1} + K_{2i}.$$

Alternatively, the law of variability $U_i(P_{BF})$ of the stimulation parameter outside of the saturation ranges is of the sigmoid type:

$$U_i(P_{BF}) = K_{1i}(V_{i2} - V_{i1}) * \left(\frac{1}{1 + e^{-p\left(P_{BF} - \frac{P_{BF2} - P_{BF1}}{2}\right)}}\right) + V_{i1} + K_{2i}.$$

In both cases, the parameter $K_{1i}$, represents a proportional adjustment factor preferably having unitary value so that the maximum excursion of $P_{BF}$ corresponds to the maximum excursion of the output $V_i(P_{BF})$. In the case in which the parameter $K_{1i}$ takes on values greater than 1, an additional saturation block is foreseen in order to ensure that the stimulation parameter $V_i$ is kept within the predetermined stimulation range. In the sole case of sigmoid function, the parameter p is adjusted based on the desired value of the function $U_i(P_{BF})$ around the point $P_{GF2}$ and $P_{BF1}$.

Specifically, since deep brain stimulation uses a stimulus defined by three stimulation parameters $V_a$, $V_d$, $V_f$ relative, respectively, to amplitude, duration and frequency of the stimulation signal $V_{stim}$, the control module 20 foresees to implement a respective law of variability $V_a(P_{BF})$, $V_d(P_{BF})$, $V_f(P_{BF})$ for each stimulation parameter $V_a$, $V_d$, $V_f$. The stimulation signal $V_{stim}$ in output from the stimulation module 16 is characterised by the parameters $V_a$, $V_d$, $V_f$, calculated based on the respective output of the control module 20.

Advantageously, the time constant T based on which the integration of the spectral power $P_{BF}$ takes place, is selected as a function of the control requirements: the greater the time constant T the smaller the variance on the evaluation of the spectral power $P_{BF}$ of the acquired signal and therefore on the instantaneous clinical state of the patient. However, increasing the time constant T increases the delay in identifying the clinical state of the patient.

Preferably, the control allows variable setting of the time constant T, so that the most suitable time constant can be set each time based on the specific application, taking into account the compromise between speed and accuracy of detection of the power.

The adjuster implemented by the control module 20 is characterised by a wide degree of flexibility thanks to the possibility of calibrating the adjustment parameters $K_{1i}$, $K_{2i}$ $P_{BF2}$, $P_{BF1}$, $\tau$, $V_{i1}$ $V_{i2}$. It is thus possible to carry out a vast range of adjustment strategies.

Figure 2:
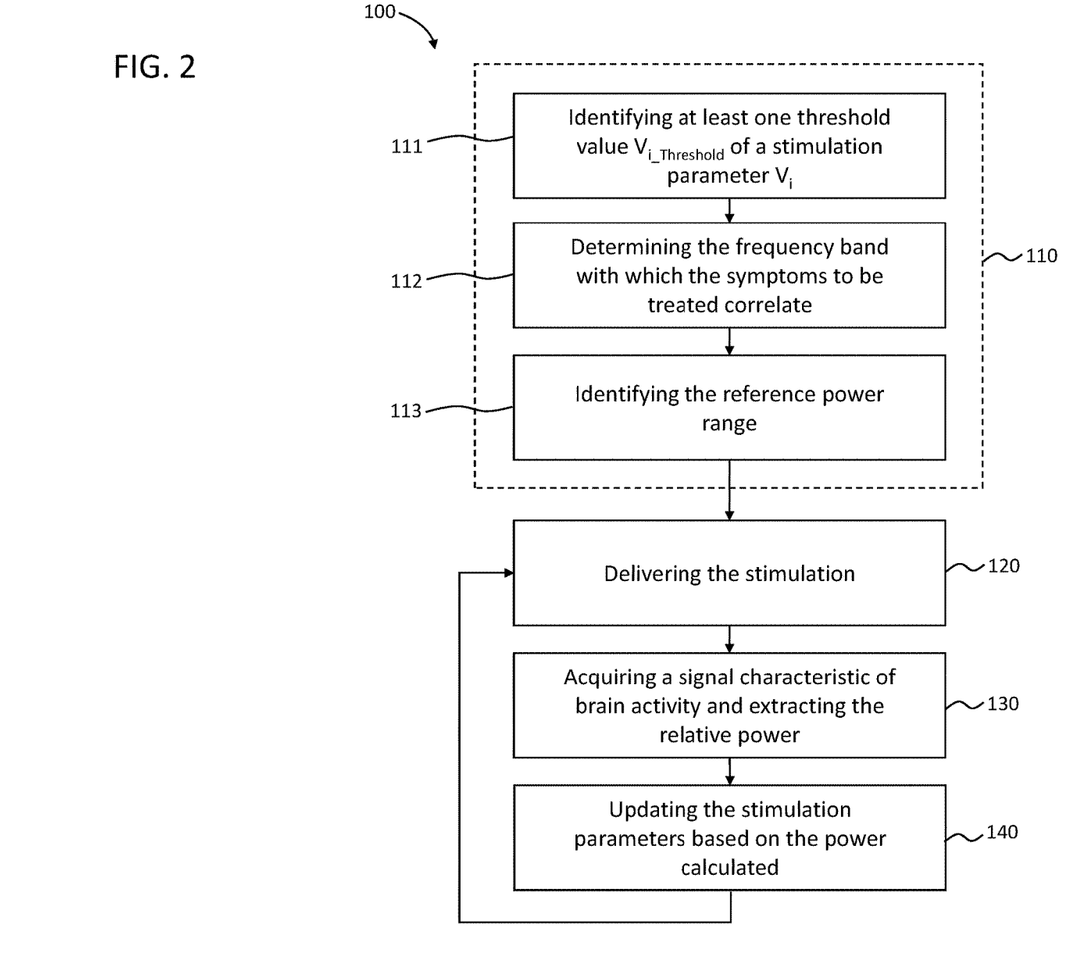
FIG. 2 is a block diagram of the main steps of the method for treating neurological disorders in accordance with the present invention.

The operating method 100 of the apparatus for treating neurological disorders 10 is schematically illustrated in FIG. 2.

Prior to the stimulation treatment there is an initialisation session (step 110). The initialisation session is carried out after the patient has spent a sufficient time (generally 12 hours) without pharmacological medication. After such a time period without pharmacological therapy, the patient is considered to be in the so-called "OFF-OFF" or base clinical condition, i.e. in the absence of stimulation and with effect of pharmacological therapy having worn off.

Then there is the identification (step 111) of at least one of the threshold values of the specific stimulation parameters of the patient based on which to set the treatment. In particular, in simplifying terms, the amplitude of the stimulation voltage is identified.

Such identification takes place through an expert, like for example a neurologist specialised in the treatment of neurological disorders through deep brain stimulation. The step of identifying the parameters (step 111) therefore takes place through a series of stimulation tests with different parameter values, based on which the expert decides the maximum threshold value $V_{i\_HighThreshold}$, to obtain the maximum clinical effect before the appearance of side effects, and minimum threshold value $V_{i\_LowThreshold}$, to obtain the minimum or zero clinical effect. The saturation values of the stimulation parameters $V_{i2}$ and $V_{i1}$ can be placed equal, respectively, to the maximum threshold value $V_{i\_HighThreshold}$ and minimum threshold value $V_{i\_LowThreshold}$ or alternatively, respectively equal to the minimum threshold value $V_{i\_LowThreshold}$ and maximum threshold value $V_{i\_HighThreshold}$.

In the case in which the parameter analysed is the amplitude $V_a$ of the stimulation signal $V_{stim}$, the step of identifying the stimulation parameters leads to determining the maximum and minimum amplitude of the voltage that can be set $V_{a\_HighThreshold}$ and $V_{a\_LowThreshold}$. Similarly, the maximum/minimum frequency and/or the maximum/minimum duration of the stimulation signal $V_{stim}$ can be identified.

Then there is a recording (step 112) of the neurophysiological signal: the harmonic content of the neurophysiological signal of the specific patient in the absence of stimulation is detected and analysed to identify the characteristics of the specific frequency spectrum of the patient. In particular, at least one frequency peak is identified, with respect to which the at least one frequency band BF is centred based on which to calculate the spectral power of the signal. The frequency bands are defined through a minimum frequency and a maximum frequency: fw_min<BF<fw_max and correspond to the frequency bands with which the symptoms of the neurological disorders that it is wished to counteract most probably correlate. The frequencies fw_min and fw_max can be selected arbitrarily.

Once the stimulation parameters and the frequency band have been defined, there is a calibration step (step 113) in which the signal characteristic of cerebral activity is recorded in a plurality of different conditions to extract the values of the power in the frequency band defined previously. Specifically, for the calibration step (step 113), the neurophysiological signal of the patient at the base state is detected, i.e. in the absence of therapies of any kind (pharmacological or stimulation) also called OFF-OFF state, and the power in the band of interest is stored. The recording of the neurophysiological signal at the OFF-OFF state takes place for an initial period, in general equal to 20 minutes. Once the initial period has ended, the stimulation is brought to the maximum threshold stimulation values $V_{i\_HighThreshold}$ determined previously. The processing and stimulation device proceeds to store the power of the signal characteristic of cerebral activity of the patient in the clinical OFF-ON state, i.e. in the absence of pharmacological therapy (LEVOdopamine), but in the presence of stimulation. After a further time period, in general equal to another 20 minutes, the pharmacological therapy is started again proceeding to store the power. After a third time period, the drug taken is considered to be completely assimilated and the patient is in the clinical ON-ON state, i.e. in the presence of pharmacological therapy and of stimulation. The storage of the power of the signal characteristic of cerebral activity of the patient is therefore ended.

Once the storage has ended, in the three initialisation steps 110, of the power calculated in the frequency band identified initially, the maximum power value $P_{BF2}$ and minimum power value $P_{BF1}$ are extrapolated.

Figure 4A:
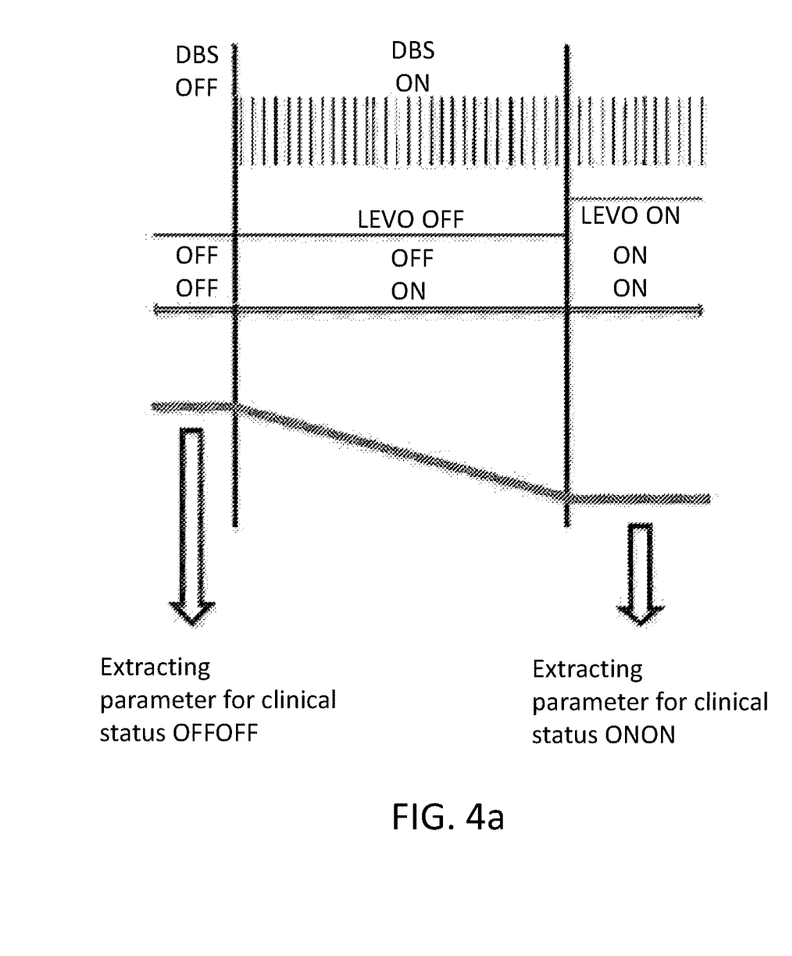
FIG. 4a is a diagram of the variation in power in beta band during the calibration step of the maximum and minimum spectral power thresholds in the case of Parkinson's disease.

In the specific case illustrated in FIG. 4a, relative to a frequency band of interest coinciding with a sub-band of the beta band (10-35 Hz), the maximum power value $P_{BF2}$ coincides with the power value in the OFF-OFF state ($N_{\beta OFFOFF}$), whereas the minimum power value $P_{BF1}$ coincides with the power value in the ON-ON state ($N_{\beta ONON}$).

Figure 4B:
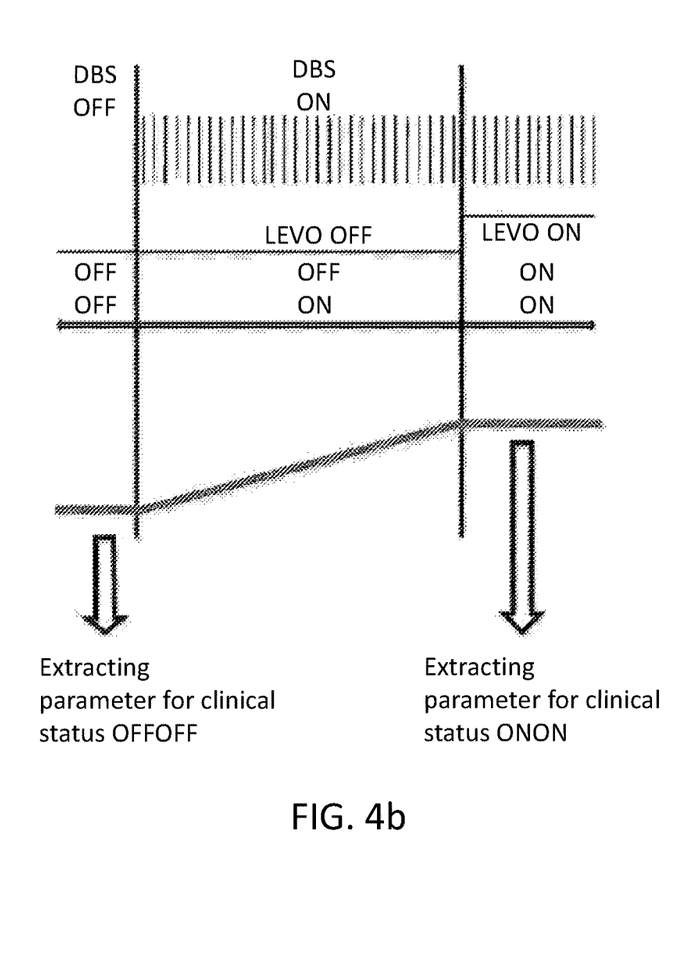
FIG. 4b is a diagram of the variation in spectral power at the low frequencies during the calibration step of the maximum and minimum spectral power thresholds in the case of Parkinson's disease.

In example terms, the case is also shown in which the frequency band of interest coincides with the low frequencies (4-10 Hz). In this case, as shown in FIG. 4b, the minimum power value $P_{BF1}$ coincides with the power value in the OFF-OFF state ($P_{lowOFFOFF}$), whereas the maximum power value $P_{BF2}$ coincides with the power value at the ON-ON state ($P_{lowONON}$).

Once the initialisation step 110 of the therapy has ended, the method 100 for treating neurological disorders comprises the repetition of the following steps.

The delivery of the deep brain stimulation is started (step 120).

Thereafter (step 130), the acquisition module 18 records a signal characteristic of cerebral activity of the patient (sub-step 131), preferably the local field potentials LFP recorded at the grey nucleus, and thereafter transforms it (sub-step 132) preferably in the frequency domain, for example through FFT (Fast Fourier Transform), determining its spectral power $P_{BF}$ (sub-step 133). Preferably, the power is also integrated based on the time constant $\tau$ (sub-step 134).

Finally, based on the spectral power $P_{BF}$ recorded, there is a step of updating the stimulation parameters (step 140).

For this purpose, the control module 20 preferably compares the power $P_{BF}$ with a range of reference values $[P_{BF2}; P_{BF1}]$ that correlate more with the band of interest. Based on the difference between the power $P_{BF}$ calculated and the lower limit $P_{BF1}$ of such a reference range $[P_{BF2}; P_{BF1}]$ a control signal for a stimulation module (16) is generated which sets the stimulation parameters ($V_a$, $V_d$, $V_f$) according to the law of variability $V_i(P_{BF})$ given above.

In the case in which the frequency band of interest coincides with a sub-band of the beta band (10-35 Hz) that, as will be seen hereinafter, proves particularly suitable for the treatment of some symptoms of Parkinson's disease, the upper extreme $P_{BF2}$ of the range of values is equal to the power $P_{\beta OFFOFF}$ at the OFF-OFF state and the lower extreme $P_{BF1}$ of the range of values is equal to the power $P_{\beta ONON}$ at the ON-ON state determined in the initialisation step, with $P_{BF2} > P_{BF1}$.

In example terms, the case is now discussed in which the treatment method according to the invention is specifically used for treating clinical-motor functions of Parkinson's disease that most correlate with the beta band β, which has therefore been identified as the reference frequency band BF based on which to calculate the spectral power of the acquired local field potentials. For this treatment it has also proven sufficient to carry out an adaptation of just the stimulation amplitude $V_a$.

In this case, the law of variability takes the form:

$$U_i(P_{BF}) = K_{1i} \frac{V_{i2} - V_{i1}}{P_{BF2} - P_{BF1}} (P_{BF} - P_{BF1}) + V_{i1} + K_{2i}$$

With the adjustment parameters $K_{1i}$, $P_{BF2}$, $P_{BF1}$, $V_{i1}$, $V_{i2}$, $K_{2i}$ equal to:

$P_{BF} = P_\beta$;
$P_{BF2} = P_{\beta OFFOFF}$
$P_{BF1} = P_{\beta ONON}$
$V_{i2} = V_{a\_HighThreshold}$
$V_{i1} = V_{a\_LowThreshold}$
$K_{1i} = K_a = 1$
$K_{2i} = 0$ In the case of the treatment of the symptoms of Parkinson's disease that correlate with the beta band, there is therefore a simplified adjustment model based on the following law of variability:

$$V_a(P_g) = sat(P_g)$$

$$= \begin{cases} V_{a\_HighThreshold} & \text{for } P_\beta \geq P_{\beta OFFOFF} \\ \frac{V_{a\_HighThreshold} - V_{a\_LowThreshold}}{P_{\beta OFFOFF} - P_{\beta ONON}} (P_g - P_{\beta ONON}) + V_{a\_LowThreshold} & \text{for } P_{\beta OFFOFF} > P_\beta > P_{\beta ONON} \\ V_{a\_LowThreshold} & \text{for } P_\beta \leq P_{\beta ONON} \end{cases}$$

Alternatively, the case is now discussed in which the treatment method according to the invention is specifically used for the treatment of the clinical-motor fluctuations of Parkinson's disease that most correlate with the band of low frequencies (4-10 Hz), which has therefore been identified as reference frequency band BF based on which to calculate the spectral power of the acquired local field potentials. For this treatment it also proved sufficient to carry out an adaptation of just the stimulation amplitude $V_a$.

In this case, the law of variability takes the form $$U_i(P_{BF}) = K_{1i}\frac{V_{i2} - V_{i1}}{P_{BF2} - P_{BF1}}(P_{BF2} - P_{BF1}) + V_{i1} + K_{2i}.$$

$$V_a(P_{low}) = sat(P_{low})$$

$$= \begin{cases} V_{a_{LowThreshold}} & \text{for } P_{low} \geq P_{lowONON} \\ \frac{V_{a_{LowThreshold}} - V_{a_{HighThreshold}}}{P_{lowONON} - P_{lowOFFOFF}}(P_{low} - P_{lowOFFOFF}) + V_{a_{HighThreshold}} & \text{for } P_{lowOFFOFF} > P_{low} > P_{lowONON} \\ V_{a_{HighThreshold}} & \text{for } P_{low} \leq P_{lowOFFOFF} \end{cases}$$

From the description that has been made the characteristics of the apparatus and of the method for treating neurological disorders object of the present invention are clear, just as the relative advantages are also clear.

From the embodiments described above further variants are possible, without departing from the teaching of the invention.

Finally, it is clear that an apparatus and a method for treating neurological disorders thus conceived can undergo numerous modifications and variants, all of which are covered by the invention; moreover, all of the details can be replaced by technically equivalent elements. In practice, the materials used, as well as the sizes, can be whatever according to the technical requirements.

The invention claimed is:

1. An apparatus for treating neurological disorders comprising:
   an electrode implantable in a patient;
   a processing and stimulation device connected to the electrode, wherein the processing and stimulation device comprises:
   a stimulation module adapted to generate a stimulation signal ($V_{stim}$) to be sent to the electrode, the stimulation signal ($V_{stim}$) having a plurality of stimulation parameters including a stimulation amplitude, stimulation duration, and stimulation frequency ($V_a$, $V_d$, $V_f$),
   an acquisition module configured to acquire neural activity signals from the patient and to calculate a power ($P_{BF}$) of a beta frequency band of the acquired neural activity signals, and
   a control module configured to:
   adjust a stimulation parameter ($V_a$, $V_d$, $V_f$) of the stimulation signal ($V_{stim}$) when the power ($P_{BF}$) of the beta frequency band meets or exceeds an upper power value threshold ($P_{BF2}$), wherein the upper power value threshold ($P_{BF2}$) is a power of the beta frequency band of the patient's neural activity signals measured in the absence of pharmacological therapy ($P_{OFF}$);

With the adjustment parameters $K_{1i}$, $P_{BF2}$, $P_{BF1}$, $V_{i1}$, $V_{i2}$, $K_{2i}$ equal to:

$P_{BF} = P_{low}$ $P_{BF2} = P_{lowONON}$ $P_{BF1} = P_{lowOFFOFF}$ $V_{i2} = V_{a\_LowThreshold}$ $V_{i1} = V_{a\_HighThreshold}$ $K_{1i} = K_a = 1$ $K_{2i} = 0$ In the case of treatment of the symptoms of Parkinson's disease that correlate most with the low frequencies, there is therefore a simplified adjustment model defined by the following law of variability:

adjust the stimulation parameter ($V_a$, $V_d$, $V_f$) of the stimulation signal ($V_{stim}$) when the power ($P_{BF}$) of the beta frequency band is at or below a lower power value threshold ($P_{BF1}$), wherein the lower power value threshold ($P_{BF1}$) is a power of the beta frequency band of the patient's neural activity signals measured in the presence of pharmacological therapy ($P_{ON}$); and adjust the stimulation parameter ($V_a$, $V_d$, $V_f$) of the stimulation signal ($V_{stim}$) according to a piecewise transfer function based on the power ($P_{BF}$) of the beta frequency band, wherein the piecewise transfer function is:

$$V_{a,d,f}(P_{BF}) = \begin{cases} V_{i\_HighThreshold} & \text{per } P_{BF} \geq P_{OFFOFF} \\ U_i(P_{BF}) & \text{per } P_{OFFOFF} > P_{BF} > P_{ONON} \\ V_{i\_LowThreshold} & \text{per } P_{BF} \leq P_{ONON} \end{cases}$$

where:
$V_{i\_HighThreshold}$ is a maximum value of the stimulation parameter that provides a maximum clinical effect before side effects appear,
$V_{i\_LowThreshold}$ is a minimum value of the stimulation parameter that provides a minimum clinical effect,
$P_{OFFOFF}$ is a power of the beta frequency band of the patient's neural activity signals measured in the absence of pharmacological therapy and in the absence of electrical stimulation,
$P_{ONON}$ is a power of the beta frequency band of the patient's neural activity signals measured in the presence of pharmacological therapy and in the presence of electrical stimulation, and
$U_i(P_{BF})$ is a law of variability that correlates a value of the stimulation parameter with the power ($P_{BF}$) of the beta frequency band.

2. The apparatus of claim 1, wherein when the power ($P_{BF}$) of the beta frequency band meets or exceeds the upper power value threshold ($P_{BF2}$), a stimulation parameter of the stimulation signal ($V_{stim}$) is set to a maximum value ($V_{i\_HighThreshold}$) of the stimulation parameter that provides a maximum clinical effect before side effects appear.

3. The apparatus of claim 1, wherein when the power ($P_{BF}$) of the beta frequency band is at or below the lower power value threshold ($P_{BF1}$), a stimulation parameter of the stimulation signal ($V_{stim}$) is set to a minimum value ($V_{i\_LowThreshold}$) of the stimulation parameter that provides a minimum clinical effect.

4. The apparatus of claim 1, wherein the upper power value threshold ($P_{BF2}$) is a power of the beta frequency band of the patient's neural activity signals measured in the absence of pharmacological therapy and in the absence of electrical stimulation ($P_{OFFOFF}$).

5. The apparatus of claim 4, wherein the lower power value threshold ($P_{BF1}$) is a power of the beta frequency band of the patient's neural activity signals measured in the presence of pharmacological therapy and in the presence of electrical stimulation ($P_{ONON}$).

6. The apparatus of claim 5, wherein when the power ($P_{BF}$) of the beta frequency band meets or exceeds $P_{OFFOFF}$, a stimulation parameter of the stimulation signal is set to a maximum value ($V_{i\_HighThreshold}$) of the stimulation parameter that provides a maximum clinical effect before side effects appear.

7. The apparatus of claim 6, wherein when the power ($P_{BF}$) of the beta frequency band is at or below $P_{ONON}$, a stimulation parameter of the stimulation signal is set to a minimum value ($V_{i\_LowThreshold}$) of the stimulation parameter that provides a minimum clinical effect.

8. The apparatus of claim 1, wherein the law of variability $U_i(P_{BF})$ is:

$$U_i(P_{BF}) = \left( \frac{V_{i\_HighThreshold} - V_{i\_LowThreshold}}{P_{OFFOFF} - P_{ONON}} \right)(P_{BF} - P_{ONON}) + V_{i\_LowThreshold}.$$

* * * * *